United States Patent
Lemoult et al.

(10) Patent No.: US 9,196,960 B2
(45) Date of Patent: Nov. 24, 2015

(54) SYSTEM FOR ILLUMINATING AN OBJECT WITH A WAVE OR FOR IMAGING AN OBJECT WITH A WAVE

(75) Inventors: Fabrice Lemoult, Paris (FR); Geoffroy Lerosey, Paris (FR); Julien De Rosny, Nogent sur Marne (FR); Ourir Abdel Waheb, Paris (FR); Mathias Fink, Meudon (FR)

(73) Assignee: Centre National de la Recherche Scientifique—CNRS, Paris (FR)

( * ) Notice: Subject to any disclaimer, the term of this patent is extended or adjusted under 35 U.S.C. 154(b) by 648 days.

(21) Appl. No.: 13/579,808

(22) PCT Filed: Feb. 22, 2010

(86) PCT No.: PCT/IB2010/000626
§ 371 (c)(1),
(2), (4) Date: Aug. 17, 2012

(87) PCT Pub. No.: WO2011/101702
PCT Pub. Date: Aug. 25, 2011

(65) Prior Publication Data
US 2012/0327744 A1    Dec. 27, 2012

(51) Int. Cl.
*B01J 19/12* (2006.01)
*G01S 15/08* (2006.01)
(Continued)

(52) U.S. Cl.
CPC *H01Q 3/46* (2013.01); *B82Y 20/00* (2013.01); *B82Y 35/00* (2013.01);
(Continued)

(58) Field of Classification Search
CPC .... B82Y 20/00; B82Y 35/00; H01Q 15/0086; H01Q 3/46; H01Q 15/10; H01Q 19/062; G01Q 60/22

USPC ........................................................ 367/140
See application file for complete search history.

(56) References Cited

U.S. PATENT DOCUMENTS 8,102,328 B2 * 1/2012 Fink et al. .................... 343/837
2009/0309805 A1 12/2009 Fink et al.
(Continued)

FOREIGN PATENT DOCUMENTS

DE  10 2007 016588    9/2008
GB       2 382 230    5/2003
(Continued)

OTHER PUBLICATIONS

International Search Report from corresponding International Patent Application No. PCT/IB2010/000626 Report Dated Aug. 26, 2010.
(Continued)

*Primary Examiner* — Daniel Pihulic
(74) *Attorney, Agent, or Firm* — Miller, Matthias & Hull LLP (57) ABSTRACT

A system for illuminating an object with a wave or for imaging an object with a wave comprises a lens, a plurality of transducers and a control unit connected to the plurality of transducers. The lens comprises a plurality of resonator elements incorporated inside a medium and is able to convert a near field wave of the lens to a far field wave, or reciprocally. The resonator elements are at a sub wavelength distance from each others. The control unit provides signals to the transducers so that a plurality of points on the object are illuminated as desired, or obtains signals from the transducers to build an image of a plurality of points of the object. The points are at sub wavelength distance from each others.

38 Claims, 3 Drawing Sheets

(51) Int. Cl.
| | |
|---|---|
| H01L 27/146 | (2006.01) |
| H01Q 3/46 | (2006.01) |
| B82Y 20/00 | (2011.01) |
| B82Y 35/00 | (2011.01) |
| G01N 29/06 | (2006.01) |
| G01Q 60/22 | (2010.01) |
| H01Q 15/10 | (2006.01) |
| H01Q 19/06 | (2006.01) |
| H01Q 15/00 | (2006.01) |

(52) U.S. Cl.
CPC ........... *G01N 29/0681* (2013.01); *G01Q 60/22* (2013.01); *H01Q 15/0086* (2013.01); *H01Q 15/10* (2013.01); *H01Q 19/062* (2013.01)

(56) References Cited

U.S. PATENT DOCUMENTS

2010/0072353 A1* 3/2010 Tschekalinskij et al. ..... 250/234
2012/0327744 A1* 12/2012 Lemoult et al. ................. 367/99

FOREIGN PATENT DOCUMENTS

WO  WO 2008/007024 A1  1/2008
WO  WO 2011101702 A1 *  8/2011

OTHER PUBLICATIONS

Belov, Pavel A., et al., "Sub-wavelength Microwave Imaging by a Slab of Wire Medium", Microwave Conference 2000, pp. 1331-1332.
Fink, Mathias, et al., "Time-reversed waves and super-resolution", Comptes Rendus—Physique, pp. 447-463, XP026600626 ISSN: 1631-0705, retrieved on Aug. 22, 2009.
Wang, Gang, et al., "On the Use of LHM Lens for Near-Field Target Detection and Imaging", Antennas, Propagation & EM Theory, 2006 ISAPE.
Lerosey, Geoffroy, et al., "Focusing beyond the diffraction limit with farfield time reversal", Science, 2007, p. 1120, vol. 315.
Lemoult, Fabrice, et al., "Resonant Metalenses for Breaking the Diffraction Barrier", Physical Review Letters, May 21, 2010, pp. 203901-1-203901-4.

* cited by examiner

SYSTEM FOR ILLUMINATING AN OBJECT WITH A WAVE OR FOR IMAGING AN OBJECT WITH A WAVE

CROSS-REFERENCE TO RELATED APPLICATIONS

This application is a 35 USC §371 U.S. national stage filing of International Patent Application No. PCT/IB2010/000626 filed on Feb. 22, 2010.

FIELD OF THE DISCLOSURE

The present invention concerns a system for illuminating an object with a wave or for imaging an object with a wave.

BACKGROUND OF THE DISCLOSURE

It is known from the applicant's own patent application WO-2008/007024, a device having a reactive type antenna element surrounded by a plurality of metallic diffusers. Thanks to this arrangement, the electromagnetic wave is focused to a point i near the antenna element at a sub wavelength distance.

This device is efficient, but is limited to the focalisation of a wave to the core of the reactive antenna element, that is to say to only one single point at a short distance from the metallic diffusers.

SUMMARY OF THE DISCLOSURE

One object of the present invention is to provide a system for illuminating an object with a wave, said object being at a sub wavelength distance from the lens of the system.

To this effect, the system for illuminating an object with a wave comprises:
  a lens for converging a far field wave to a near field wave, said lens comprising a medium and a plurality of resonator elements incorporated inside said medium, each resonator element being spaced from an other resonator element inside the medium of a distance lower than a first distance $d_1$, and having:
    a width $w_R$ in a direction to a neighbour resonator element lower than said first distance $d_1$,
    a length $l_R$ in an other direction, and
    a resonance frequency $f_R$ corresponding to a resonance wavelength $\lambda_R$,
  a plurality of transducers remote from said lens, said plurality of transducers having a transducer wavelength bandwidth $\Delta\lambda_T$ and being adapted to emit the far field wave towards the lens based on signals $t_j(t)$ of index-number j, and
  a control unit connected to said transducers, said control unit providing signals $t_j(t)$ of index-number j to the transducers so that the transducers emit a far field wave corresponding to the signals and so that the lens produces a desired near field wave, said desired near field wave being focused on at least a plurality of points $P_i$ of index-number i belonging to an object so as to illuminate said object with said desired near field wave,
wherein:
  the resonance wavelength $\lambda_R$ is comprised between $\lambda_{min}$ and $\lambda_{max}$ inside the transducer wavelength bandwidth $\Delta\lambda_T$ so that the near field wave spreads into a desired wavelength bandwidth $\Delta\lambda_D$ between $\lambda_{min}$ and $\lambda_{max}$,
  the first distance $d_1$ is lower than $\lambda_{max}/5$ so that said resonator elements are coupled to each other, and the system further comprises positioning means adapted for positioning at least one point $P_i$ of the object at a distance of at least one resonator element lower than a second distance $d_2$, said second distance $d_2$ being lower than $\lambda_{max}/5$.

Thanks to these features, the system may illuminate a plurality of points $P_i$ on an object positioned at a short sub wavelength distance from the lens.

In various embodiments of the system for illuminating, one and/or other of the following features may optionally be incorporated:
  the desired near field wave is focused simultaneously on said plurality of points;
  the width $w_R$ is lower than $d_1/5$, and preferably lower than $d_1/20$;
  the first distance $d_1$ is lower than $\lambda_{max}/20$, and preferably lower than $\lambda_{max}/50$;
  the second distance $d_2$ is lower than $\lambda_{max}/20$, and preferably lower than $\lambda_{max}/50$;
  the length $l_R$ of the resonator element is roughly equal to $\lambda_R/2$ or a multiple of it;
  the resonator elements have a plurality of lengths so that the lens has a plurality of resonance wavelengths $\lambda_R$ between $\lambda_{min}$ and $\lambda_{max}$;
  the system further comprises at least one lens transducer incorporated inside said lens, wherein said lens transducer is fed with a lens signal l(t), the control unit is connected to said lens transducer and provide the lens signal l(t);
  the control unit computes the signals $t_j(t)$ of the transducer of index-number j by one of the following formulas:

$t_j(t) = h_{ij}^{-1}(t) * o_i(t)$ in time domain, and $t_j(t) = IFFT(H_{ij}^{-1}(\omega) \cdot O_i(\omega))$ frequency domain, where
$o_i(t)$ is an object signal corresponding to the desired near field wave on the object,
$h_{ij}(t)$ are predetermined filters designed to focus the near field wave on the point of index-number i of the object,
t is a time value,
* is the convolution product operator,
$O_i(\omega)$ is a Fourier transform of the object signal $o_i(t)$,
$H_{ij}(\omega)$ is a Fourier transform of the predetermined filters $h_{ij}(t)$,
IFFT is an inverse Fourier transform, and
$\omega$ is a frequency pulsation equal to $2.\pi.f$ where f is a frequency of the desired near field wave;
  the predetermined filters $h_{ij}(t)$ are one of:
    delay filters so that the control unit computes beamforming formulas; and
    filters determined on basis of an impulse response $g_{ij}(t)$ between the point of index-number i of the object and the transducer of index-number j; and
    temporal inversion $g_{ij}(-t)$ of an impulse response $g_{ij}(t)$ between the point of index-number i of the object and the transducer of index-number j;
  the impulse response $g_{ij}(t)$ is determined during an initial learning step wherein at least one calibration transducer is positioned in the place of the object at each of said points of index-number i and at least a calibration signal is exchanged between said calibration transducer and the transducer of index-number j;
  the impulse response $g_{ij}(t)$ is determined during an initial learning step wherein a simulation tools running on a computer is filled in with a model of the system and wherein said model comprises at least one calibration transducer positioned in the place of the object at each of said points of index-number i and at least a calibration signal is exchanged between said calibration transducer and the transducer of index-number j;

the transducers are electromagnetic antenna elements adapted to emit an electromagnetic far field wave and the resonator elements are conductive wires adapted to receive an electromagnetic far field wave and to emit an electromagnetic near field wave;

the transducers are photo emitters adapted to emit a far field wave of light and the resonator elements are conductive elements adapted to receive said far field wave of light and to emit a near field wave of light;

the conductive elements are nanoparticles or conductor elements having a width $w_R$ lower than 50 nm;

the conductive elements comprise active materials adapted to receive a wave at a first wavelength $\lambda_1$ and to emit a wave at a second wavelength $\lambda_2$ different to said first wavelength $\lambda_1$;

said active materials are one of quantum dots, and dyes, and fluorescent molecules.

Another object of the present invention is to provide a system for imaging an object with a wave, said object being at a sub wavelength distance from the lens of the system.

To this effect, the system for imaging an object with a wave comprises:

a lens for diverging a near field wave to a far field wave, said lens comprising a medium and a plurality of resonator elements incorporated inside said medium, each resonator element being spaced from an other resonator element of a distance lower than a first distance $d_1$, and having:

a resonance frequency $f_R$ corresponding to a resonance wavelength $\lambda_R$, a width $w_R$ in a direction to a neighbour resonator element lower than said first distance $d_1$, and a length $l_R$ in an other direction, a plurality of transducers remote from said lens, said plurality of transducers having a transducer wavelength bandwidth $\Delta\lambda_T$ and being adapted to receive the far field wave from the lens and to provide signals $t_j(t)$ of index-number j representative to said far field wave, and a control unit connected to said transducers, said control unit being fed with the signals $t_j(t)$ of index-number j from the transducers, and adapted to determine therewith the near field wave at a plurality of points $P_i$ of index-number i belonging to an object so as to obtain an image of said object, wherein:

the resonance wavelength $\lambda_R$ is comprised between $\lambda_{min}$ and $\lambda_{max}$ inside the transducer wavelength bandwidth $\Delta\lambda_T$, so that the far field wave spreads into a desired wavelength bandwidth $\Delta\lambda_D$ between $\lambda_{min}$ and $\lambda_{max}$, the first distance $d_1$ is lower than $\lambda_{max}/5$ so that the resonator elements are coupled to each other, and the system further comprises positioning means adapted for positioning at least one point of the object at a distance of at least one resonator element lower than a second distance $d_2$, said second distance $d_2$ being lower than $\lambda_{max}/5$.

Thanks to these features, the system may provide an image of a plurality of points $P_i$ on an object positioned at a short sub wavelength distance from the lens.

In various embodiments of the system for imaging proposed by the invention, one and/or the other of the following features may optionally be incorporated:

the near field wave is determined simultaneously on said plurality of points;

the width $w_R$ is lower than $d_1/5$, and preferably lower than $d_1/20$;

the first distance $d_1$ is lower than $\lambda_{max}/20$, and preferably lower than $\lambda_{max}/50$;

the second distance $d_2$ is lower than $\lambda_{max}/20$, and preferably lower than $\lambda_{max}/50$;

the length $l_R$ of the resonator element is roughly equal to $\lambda_R/2$ or a multiple of it;

the resonator elements have a plurality of lengths so that the lens has a plurality of resonance wavelengths $\lambda_R$ between $\lambda_{min}$ and $\lambda_{max}$;

the system further comprises emitting means for emitting an emitted wave having wavelengths comprised between $\lambda_{min}$ and $\lambda_{max}$ towards said object, so that a near field wave is refracted or reflected from said object, said near field wave comprising wavelengths comprised between $\lambda_{min}$ and $\lambda_{max}$ and being diverged by the lens into a far field wave;

the system further comprises emitting means connected to said object, so that the object itself emits a near field wave comprising wavelengths comprised between $\lambda_{min}$ and $\lambda_{max}$ and being diverged by the lens into a far field wave;

the system further comprises at least one lens transducer incorporated inside said lens, wherein said lens transducer is fed with a lens signal l(t), the control unit is connected to said lens transducer and provide the lens signal l(t);

the control unit:

receives signals $t_j(t)$ from the transducers, calculates object signals $o_i(t)$ at each of the points of index-number i by the following formula:

$$o_i(t) = h_{ij}(t) * t_j(t)$$

where $h_{ij}(t)$ are predetermined filters designed to determine the near field wave on the point of index-number

* is the convolution product operator, and builds an image of the object with the values at origin time $o_i(0)$ of the object signals $o_i(t)$ at each of the points of index-number l;

the predetermined filters $h_{ij}(t)$ are one of:

delay filters so that the control unit computes beamforming formulas; and filters determined on basis of an impulse response $g_{ij}(t)$ between the point of index-number i of the object and the transducer of index-number j; and temporal inversion $g_{ij}(-t)$ of an impulse response $g_{ij}(t)$ between the point of index-number i of the object and the transducer of index-number j;

the impulse response $g_{ij}(t)$ is determined during an initial learning step wherein at least one calibration transducer is positioned in the place of the object at each of said points of index-number i and at least a calibration signal is exchanged between said calibration transducer and the transducer of index-number j;

the impulse response $g_{ij}(t)$ is determined during an initial learning step wherein a simulation tools running on a computer is filled in with a model of the system and wherein said model comprises at least one calibration transducer positioned in the place of the object at each of said points of index-number i and at least a calibration signal is exchanged between said calibration transducer and the transducer of index-number j;

the transducers are electromagnetic antenna elements adapted to receive an electromagnetic far field wave and the resonator elements are conductive wires adapted to receive an electromagnetic near field wave and to emit an electromagnetic far field wave;

the transducers are photo receivers adapted to receive a far field wave of light and the resonator elements are conductive elements adapted to receive a near field wave of light and to emit a far field wave of light;

the conductive elements are nanoparticles or conductor elements having a width $w_R$ lower than 50 nm;

the conductive elements comprise active materials adapted to receive a wave at a first wavelength $\lambda_1$ and to emit a wave at a second wavelength $\lambda_2$ different to said first wavelength $\lambda_1$;

said active materials are one of quantum dots, and dyes, and fluorescent molecules.

Another object of the invention is to provide a method for illuminating an object with a wave, wherein:

resonator elements are incorporated inside a medium to form a lens for converging a far field wave to a near field wave, said resonator elements being spaced from an other resonator element inside the medium of a distance lower than a first distance $d_1$, and having:

a width $w_R$ in a direction to a neighbour resonator element lower than said first distance $d_1$, a length $l_R$ in an other direction, and a resonance frequency $f_R$ corresponding to a resonance wavelength $\lambda_R$, said resonance wavelength $\lambda_R$ being comprised between $\lambda_{min}$ and $\lambda_{max}$, and the first distance $d_1$ being lower than $\lambda_{max}/5$ so that said resonator elements are coupled to each other, at least one point $P_i$ of the object is positioned at a distance of at least one resonator element lower than a second distance $d_2$, said second distance $d_2$ being lower than $\lambda_{max}/5$, a plurality of transducers are positioned remote from said lens, said plurality of transducers having a transducer wavelength bandwidth $\Delta\lambda_T$ comprising $\lambda_{min}$ and $\lambda_{max}$, and being adapted to emit the far field wave towards the lens based on signals $t_j(t)$ of index-number j, and signals $t_j(t)$ of index-number j are provided to the transducers so that the transducers emit a far field wave corresponding to the signals and so that the lens produces a desired near field wave, said near field wave having wavelengths comprised into a desired wavelength bandwidth $\Delta\lambda_D$ between $\lambda_{min}$ and $\lambda_{max}$, and being focused on at least a plurality of points $P_i$ of index-number i belonging to said object so as to illuminate said object with said desired near field wave.

Another object of the invention is to provide a method for imaging an object with a wave, wherein:

the object emits a near field wave, and comprises resonator elements are incorporated inside a medium to form a lens for diverging the near field wave to a far field wave, said resonator elements being spaced from an other resonator element inside the medium of a distance lower than a first distance $d_1$, and having:

a width $w_R$ in a direction to a neighbour resonator element lower than said first distance $d_1$, a length $l_R$ in an other direction, and a resonance frequency $f_R$ corresponding to a resonance wavelength $\lambda_R$, said resonance wavelength $\lambda_R$ being comprised between $\lambda_{min}$ and $\lambda_{max}$, and the first distance $d_1$ being lower than $\lambda_{max}/5$ so that said resonator elements are coupled to each other, and said far field wave having wavelengths comprised into a desired wavelength bandwidth $\Delta\lambda_D$ between $\lambda_{min}$ and $\lambda_{max}$, at least one point $P_i$ of the object is positioned at a distance of at least one resonator element lower than a second distance $d_2$, said second distance $d_2$ being lower than $\lambda_{max}/5$, a plurality of transducers are positioned remote from said lens, said plurality of transducers having a transducer wavelength bandwidth $\Delta\lambda_T$ comprising $\lambda_{min}$ and $\lambda_{max}$, and being adapted to receive the far field wave from the lens and to provide signals $t_j(t)$ of index-number j representative to said far field wave, and the signals $t_j(t)$ of index-number j are provided to a control unit to determine therewith the near field wave at a plurality of points $P_i$ of index-number i belonging to an object so as to obtain an image of said object.

BRIEF DESCRIPTION OF THE DRAWINGS

Other features and advantages of the invention will be apparent from the following detailed description of two of its embodiments given by way of non-limiting examples, with reference to the accompanying drawings. In the drawings.

DETAILED DESCRIPTION OF THE DISCLOSURE

The invention concerns firstly a system for illuminating an object with a wave and secondly a system for imaging an object with a wave.

The system for illuminating an object is described bellow. The system for imaging an object will be described later in this description.

The wave may be any type of wave. It could be an acoustic wave, an electromagnetic wave, an optical wave. The system could be adapted to each type of wave, with slight differences concerning at least the transducers. The transducers are indeed usually adapted to a specific wavelength bandwidth $\Delta\lambda_T$ concerning only one of the types of waves.

Figure 1:
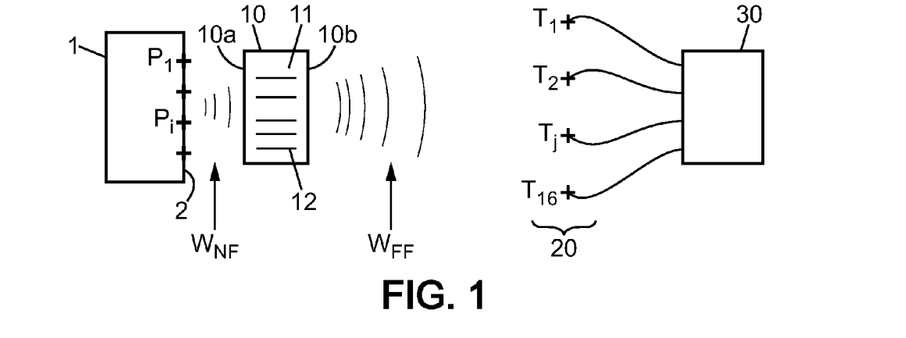
FIG. 1 is a schematic view of a system for illuminating an object, or a system for imaging an object.

A first embodiment illustrating a system adapted for an electromagnetic wave is described now, regarding the FIG. 1.

The system for illuminating an object comprises:

a lens 10 for converging a far field wave $W_{FF}$ to a near field wave $W_{NF}$, a plurality of transducers 20, said transducers being individually denoted $T_j$, j being an index-number of a transducer in the plurality, and adapted to emit the far field wave $W_{FF}$ towards the lens 10, and a control unit 30 connected to said transducers 20 and delivering a signal $t_j(t)$ to the transducer $T_j$ of index-number j.

The control unit 30 is adapted to computes the signals $t_k(t)$ based on:

a desired near field wave $W_{DNF}$ focused on an object 1, for example defined by object signals $o_i(t)$ desired at a plurality of points $P_i$, i being an index-number, and a knowledge of the system, for example predetermined filters $h_{ij}(t)$ designed to focus the near field wave $W_{NF}$ to a point $P_i$.

Each point $P_i$ belongs to a surface 2 of said object 1. Said surface 2 may be a plane surface or not.

The control unit 30 therefore computes the following formulas:

$$t_j(t)=h_{ij}^{-1}(t)*o_i(t) \text{ in time domain, or} \qquad (1)$$

$$t_j(t)=IFFT(H_{ij}^{-1}(\omega)\cdot O_i(\omega)) \text{ in frequency domain,} \qquad (2)$$

where $o_i(t)$ is an object signal corresponding to the desired near field wave on the object, $h_{ij}(t)$ are predetermined filters designed to focus the near field wave on the point of index-number i of the object, t is a time value,

* is the convolution product operator, $O_i(\omega)$ is a Fourier transform of the object signal $o_i(t)$, $H_{ij}(\omega)$ is a Fourier transform of the predetermined filters $h_{ij}(t)$, IFFT is an inverse Fourier transform, and $\omega$ is a frequency pulsation equal to $2.\pi.f$ where f is a frequency of the desired near field wave.

The predetermined filters may be determined by many known methods.

According to a first variant, the predetermined filters $h_{ij}(t)$ are delay filters so that the equation (1) corresponds to well known beam forming focussing.

According to a second variant, the predetermined filters $h_{ij}(t)$ are themselves computed with the impulse responses $g_{ij}(t)$ between the transducer j and the point $P_i$.

According to a third variant, the predetermined filters $h_{ij}(t)$ are themselves computed with the temporal inversion $g_{ij}(-t)$ of the impulse responses $g_{ij}(t)$ between the transducer j and the point $P_i$, as explained inter alia in FR-2 748 137 and in WO-2008/007024 concerning temporal inversion.

The plurality of transducers 20 are remote from the lens 20, and emit the far field wave $W_{FF}$ towards the lens 10. Each transducer $T_j$ is fed with the signal $t_j(t)$ provided by the control unit 30, so that the plurality of transducers 20 emits the far field wave $W_{FF}$.

A transducer $T_j$ of said plurality has a wavelength bandwidth $\Delta\lambda_T$.

In case of electromagnetic wave, a transducer $T_j$ is an electromagnetic antenna element. An electromagnetic wave has for example a wavelength $\lambda$ between 1 mm and 1 m, corresponding to a frequency between 300 GHz and 300 MHz.

The lens 10 comprises a medium 11 and a plurality of resonator elements 12 incorporated inside said medium 11. The medium 11 can be a solid dielectric material, and may comprise also active materials.

In case of electromagnetic wave, the resonator elements 12 are conductive wires, for example metallic or copper wires. The lens 10 may have a parallelepiped shape with a first surface 10a facing the object 1 and a second surface 10b opposite to said first surface 10a. The far field wave $W_{FF}$ propagates at least between the transducers 20 and the second surface 10b of the lens 10. The lens 10 converts the far field wave $W_{FF}$ to a near field wave $W_{NF}$. The near field wave $W_{NF}$ propagates at least between the first surface 10a of the lens 10 and the object 1.

Figure 2:
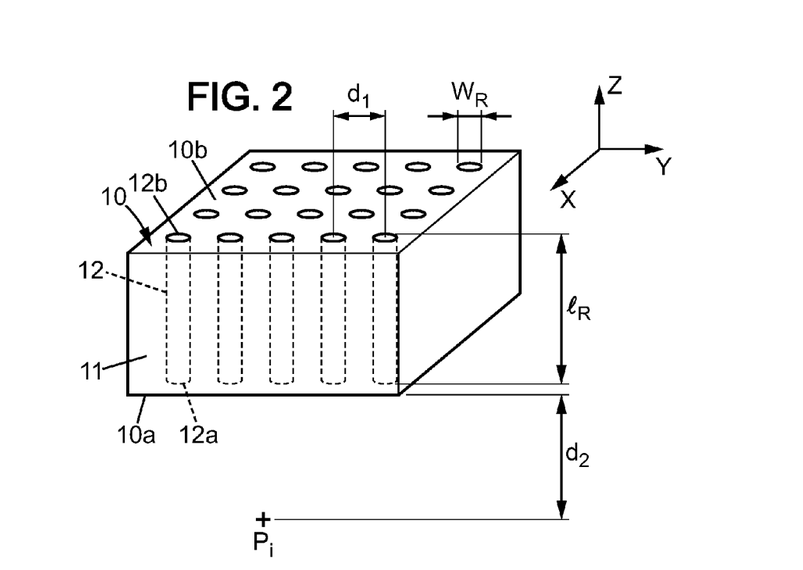
FIG. 2 is detailed view of the lens of FIG. 1.

The resonator elements 12 extend between the first surface 10a and the second surface 10b of the lens 10. They have (see FIG. 2):

a width $w_R$ in a direction to a neighbour resonator element lower than said first distance $d_1$, a length $l_R$ in an other direction, and a resonance frequency $f_R$ corresponding to a resonance wavelength $\lambda_R$.

In case of FIG. 2, the direction is a direction of the plane XY, and the other direction is direction Z.

The resonance wavelength $\lambda_R$ of a resonator element is comprised between $\lambda_{min}$ and $\lambda_{max}$, and is for example a multiple of $2.l_R$. The length $l_R$ of the resonator element 12 is roughly equal to $\lambda_R/2$ or a multiple of it, therefore corresponding to a Fabry-Perot resonance.

Figure 3:
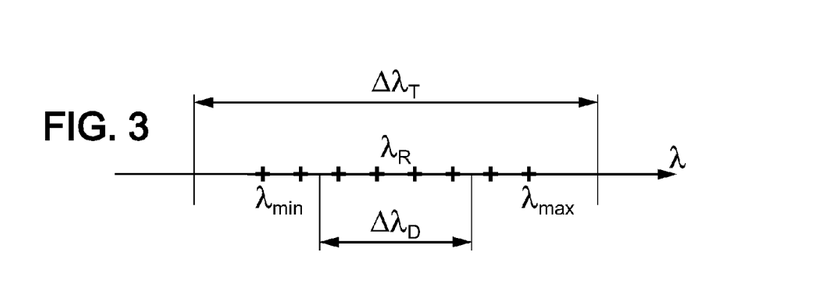
FIG. 3 is a plot for understanding the bandwidth of wavelength concerning the near field wave and the far field wave.

The resonance wavelength $\lambda_R$ is also comprised inside the transducer wavelength bandwidth $\Delta\lambda_T$ so that the near field wave $W_{NF}$ spreads into a desired wavelength bandwidth $\Delta\lambda_D$ between said $\lambda_{min}$ and $\lambda_{max}$. FIG. 3 represents these intervals of wavelengths.

The resonator elements 12 are spaced from each other of a distance lower than a first distance $d_1$. The first distance is a sub wavelength distance, usually lower than $\lambda_{max}/5$ so that said resonator elements are coupled to each other But, the first distance $d_1$ may be lower than $\lambda_{max}/20$, and preferably lower than $\lambda_{max}/50$, so that the resonator elements are very close from each other and highly coupled to each others.

The resonator elements 12 may be straight lines as represented on FIG. 2 extending from the first surface 10a to the second surface 10b in a direction Z, and regularly spaced from each other of the first distance $d_1$ in a direction X or Y. But the resonator elements 12 may have different shapes, may be inclined from each other, and may not be as regularly spaced from each other.

In the case of FIG. 2, the resonator elements 12 have a length $l_R$ in the direction Z. They have first ends 12a on the first surface 10a and second ends 12b on the second surface 10b, these surfaces 10a, 10b being planes roughly perpendicular to the direction Z. The first ends 12a and the second ends 12b form a grid of small discs on said surfaces. These discs have a width $w_R$ whose centres are spaced from a neighbour disc of distance roughly equal to the first distance $d_1$.

The width $w_R$ of the resonator element 12 is lower than $d_1/5$, and preferably lower than $d_1/20$. Consequently, the width $w_R$ of the resonator element 12 is very small and lower than $\lambda_{max}/25$, and preferably lower than $\lambda_{max}/100$.

Such lens is also known as a wire medium. In such wire medium comprising wire conductor elements 12, the magnetic field vector B and the electric field vector E are perpendicular to the direction Z, and the propagation wave vector K is a propagation vector collinear to said direction Z. Inside the wire medium, the electromagnetic wave is a plane wave propagating inside the medium 11 along the direction Z.

Figure 4A:
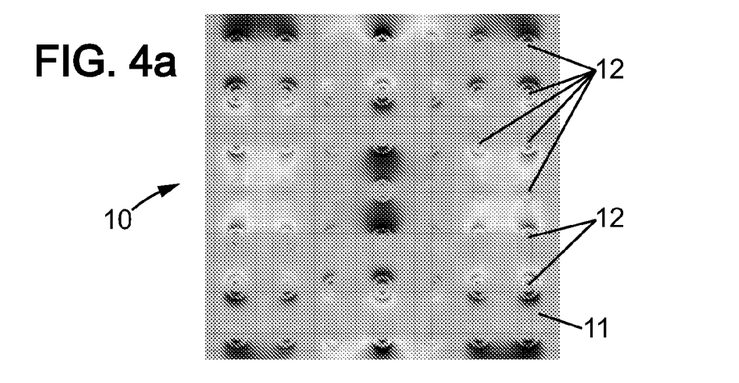
FIGS. 4a, 4b and 4c are views of three transverse electromagnetic modes inside the lens of FIG. 1.
Figure 4B:
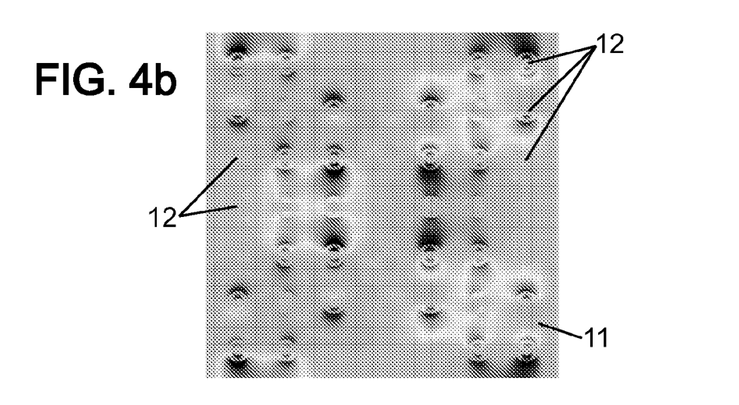
Figure 4C:
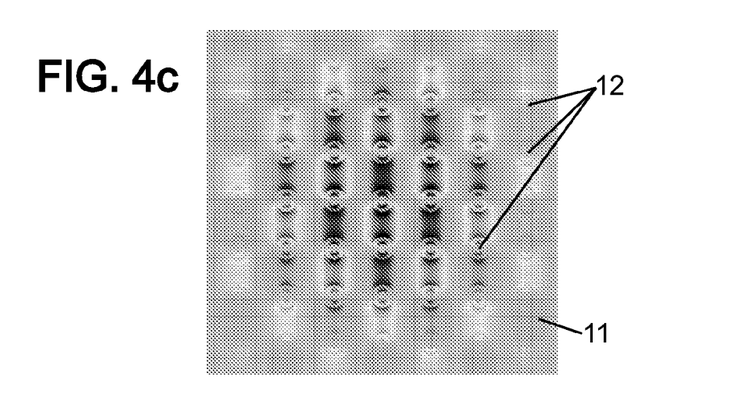

The magnetic field vector B and electric field vector E have transverse electromagnetic modes (TEM) inside said medium 11, with nodes and antinodes. These TEM modes have sub-wavelengths variations along directions X and Y. FIGS. 4a, 4b, and 4c represent an example of the amplitude variations of the electric field vector E inside the medium 11 according three different modes. Each mode has a different pattern inside the medium 11 and is orthogonal to the other modes. The Z components of the magnetic field vector B and the electric field vector E are zero inside the medium 11.

The medium 11 is therefore an anisotropic medium. Each TEM mode has the same propagation speed and the same resonance frequency. They have the same phase velocity, and the TEM modes are dispersionless.

The near field wave $W_{NF}$ decomposes onto these TEM modes with a unique set of amplitudes and phases, so that the near field wave $W_{NF}$ is converted into a unique specific spectrum inside the lens 10 and into a specific unique temporal signature of the electric field: The lens encodes the near field wave according to a unique specific way.

The near field wave space resolution is then limited by the first distance $d_1$ between the resonators and the losses inside the lens 10.

The TEM modes have a transverse wave number k and they penetrate outside of the medium up to a penetration distance $d_k$:

$$d_k = \frac{1}{\kappa} = \frac{1}{\sqrt{|k_t|^2 - |k|^2}}$$

where
$k_t$ is the transverse wave number of a TEM mode,
k is free space wave number, i.e. $k = 2.\pi.f/c$,
f is the frequency of wave, and
c is the electromagnetic wave speed in vacuum.

The length for the TEM mode propagation is not the length $l_R$ of the resonator element 12, but an effective length $L_{eff}$ which is equal to:

$$L_{eff} = \frac{2}{\kappa} + l_R$$

This effective length $L_{eff}$ may then be used to define the condition for resonance ($L_{eff} = \lambda_0/2$ for the first Fabry-Perot like condition), and gives the following dispersion relation:

$$\frac{f_0}{f} = 1 + \frac{2}{\pi} \frac{1}{\sqrt{(|k_t|/k_0)^2 - (f/f_0)^2}}$$

where
f is the resonance frequency,
$f_0$ is the Fabry-Perot resonance frequency,
$k_t$ is the transverse wave number of a TEM mode, and
$k_0$ is the Fabry-Perot wave number.

The TEM modes of the lens 10 are sub wavelength modes that only generate evanescent waves, not propagating outside of the lens to the far field.

However, the Z component $E_z$ of the electric field vector E is non zero at the longitudinal boundaries of the lens 10 (in proximity of the first surface 10a and the second surface 10b). This component $E_z$ is coupled to the internal TEM modes. It has the same periodicity than the TEM modes inside the lens 10 and radiates as the far field wave $W_{FF}$.

The coupling converts therefore the far field wave $W_{FF}$ into the near field wave $W_{NF}$ of the lens 10, and reciprocally. Such coupling or conversion is not very efficient and inversely proportional or related to the transverse wave number $k_t$. But, the TEM modes are very efficient and have a quality factor Q proportional to the same transverse wave number $k_t$. This quality factor is reduced by the losses in the lens. Then, signals transmitted from the near field wave $W_{NF}$ through the near field TEM modes inside the lens are radiated to the far field wave $W_{FF}$, and reciprocally. The coding or signature of the near field wave may be found inside the far field wave.

This explains how the near field wave $W_{NF}$ is converted into a specific electric field E inside the lens, and is then radiated out of the lens into a far field wave $W_{FF}$, free space radiation. Reciprocally, the far field wave $W_{FF}$ is transformed or converted by the lens 10 into a near field wave $W_{NF}$ inside or at proximity of the lens, by the TEM modes of the lens.

The system further comprises positioning means (not shown) adapted for positioning the object 1 relative to the lens 10, at a short sub-wavelength distance. One point $P_i$ of the surface 2 of the object 1 is therefore positioned at a second distance $d_2$ from the lens (at least a resonator element 12 of the lens). Said second distance is a sub-wavelength distance, and is lower than $\lambda_{max}/5$.

The second distance $d_2$ may be lower than $\lambda_{max}/20$, and preferably lower than $\lambda_{max}/50$, so that the points $P_i$ of the object 1 are very close to the lens 10 and are illuminated by the near field wave $W_{NF}$.

Such system for illuminating an object may focus a desired near field wave $W_{DNF}$ on an object 1 or illuminate such object 1 with said desired near field wave $W_{DNF}$. The point $P_i$ of the object 1 may be all illuminated simultaneously with a different desired near field wave $W_{DNF}$.

The points $P_i$ are at sub wavelength distance from each others, that is to say at a predetermined distance $d_p$ lower than $\lambda_{max}/20$, and preferably lower than $\lambda_{max}/50$.

An experiment was carried out to demonstrate such behaviour of the lens.

A square periodic lattice of N×N (N=20) parallel conductor wires 12 was build. Each wire has a diameter or width $w_R$ of 3 mm, a length $l_R$ of 40 cm in direction Z. The first distance $d_1$ between the wires in a transversal direction (plane XY) is of 1.2 cm. Consequently, the wire are distant from each other of a first distance lower than to $\lambda/66$. The medium 11 is air.

An antenna element (a small transverse electric dipole) is positioned at a second distance $d_2$ of 2 mm from the lens at a plurality of the points $P_i$.

During an initial learning step, the antenna element is fed with a signal consisting in a 5 ns pulse centred on around 300 MHz for each point $P_i$. The transducers signals $t_{ij}(t)$ received by the transducers 20 in the far field wave gives the impulse response $g_{ij}(t)$ ($g_{ij}(t) = t_{ij}(t)$) between the point $P_i$ and the transducer $T_j$. The decomposition of the emitted signal onto the TEM modes of the lens is unique, so that the impulse response $g_{ij}(t)$ or its Fourier transform depends on the position of the element at point $P_i$, giving a unique signature.

Figure 5:
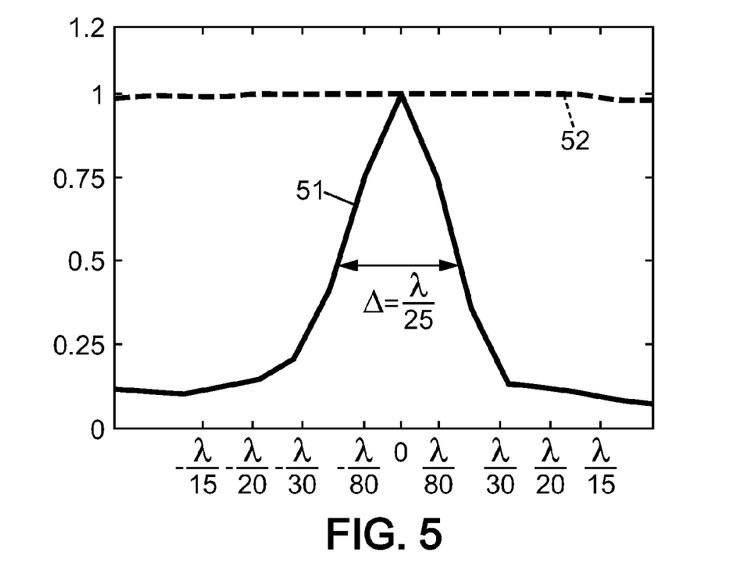
FIG. 5 is a plot concerning an illumination experience of the object by the system of FIG. 1, with and without the lens.

Then, during an illumination step, the transducers 20 are now fed with transducers signals $t_{ij}(t)$ which are the time reversal of the previous signal ($t_{ij}(t) = g_{ij}(-t)$), to carry out a time reversal experiment. The plot of FIG. 5 presents signals amplitude (ordinate or y-axis of the plot) received at a plurality of points $P_i$ (abscissa or x-axis of the plot) aligned regularly at 2 mm from the lens. The first curve 51 shows the received amplitudes with the lens.

This demonstrates that a focal spot of wavelength width $\Delta$ of $\lambda/25$ is experienced. Such focalisation of the near field wave $W_{NF}$ is therefore adapted to illuminate each point $P_i$ with a different and uncorrelated value. The second curve 52 shows the received amplitudes without the lens. In that case, there is no focalisation.

Such system for illuminating an object may then be used for transmitting precisely a plurality of data simultaneously between the far field transducers 20 and the near field object 1.

A second embodiment illustrating a system adapted for an optical wave is described now.

The system of this second embodiment is similar and works similarly to the first embodiment. Only the differences will be explained.

The transducers 20 are photo emitters adapted to emit a far field wave $W_{FF}$ of light.

The resonator elements 12 are small conductive elements having a size or width $w_R$ lower than the wavelength $\lambda$ of the far field wave $W_{FF}$, for example lower than 50 nm. Such small conductive elements also have a resonance frequency which interacts with an incident far field wave $W_{FF}$, and refracts a modified near field wave $W_{NF}$.

Such conductive elements may be nanoparticles.

The conductive element may comprise of active materials adapted to receive a wave at a first wavelength $\lambda_1$ and to emit a wave at a second wavelength $\lambda_2$ different to said first wavelength. Such active materials may be quantum dots or dyes or fluorescent molecules or the like.

Such system for illuminating an object may then be used for focalising a light wave with sub wavelength resolution, for example for a resolution lower than 20 nm, and preferably lower than 10 nm. The system may illuminate in the near field wave one single point or a plurality of points simultaneously or a complete surface with an image.

Thus, such system for illuminating an object may be used for example for etching a semiconductor device, precisely and quickly.

A third embodiment illustrating a system adapted for an acoustic wave is described now.

The acoustic sub wavelength lens 10 may be a rigid structure in air having a plurality of holes from a first side to a second side of the structure. The holes have a Helmholtz resonance and are the resonator elements 12 of the lens 10, while the rigid structure is the medium 11. For example, having a structure of 10 cm thick would provide a lens with modes around 1500 Hz.

Such acoustic lens 10 will behave like the wire media electromagnetic lens, converting the sub wave length near field wave $W_{NF}$ into a radiated far field wave $W_{FF}$ comprising the temporal and spectrum signature of the near field wave, and reciprocally.

The system for imaging an object is described now.

A first embodiment illustrating a system adapted for an electromagnetic wave is described, regarding also FIG. 1.

The system is very similar to the system for illuminating an object, the waves propagating in the reverse way. It comprises:

a lens 10 for diverging a near field wave $W_{NF}$ to a far field wave $W_{FF}$, a plurality of transducers 20, said transducers being adapted to receive the far field wave $W_{FF}$ from the lens 10, and a control unit 30 connected to said transducers and being fed with the signals $t_j(t)$ from the transducers, and adapted to determine therewith the near field wave $W_{NF}$ at a plurality of points $P_i$ belonging to an object so as to obtain an image of said object.

Each point belongs to a surface 2 of the object 1. The points $P_i$ are at sub wavelength distance from each others.

The system further comprises positioning means (not shown) adapted for positioning the object 1 relative to the lens 10 at a second distance $d_2$ from at least one resonator element 12 of the lens 10. The second distance $d_2$ is a short distance and verifies the same conditions as for the first embodiment of the invention.

The system further comprises emitting means.

According to a first variant, the near field wave $W_{NF}$ is indirectly emitted by the object 1. The emitting means emit an emitted wave towards the object 1, and a near field wave $W_{NF}$ is reflected or refracted from the object 1 towards the lens 10. The emitted wave and the near field wave comprise wavelengths between $\lambda_{min}$ and $\lambda_{max}$.

According to a second variant, the near field wave $W_{NF}$ is directly emitted by the object 1. The emitting means are connected to the object 1 and the object 1 emits itself a near field wave $W_{NF}$ having wavelengths between $\lambda_{min}$ and $\lambda_{max}$ towards the lens 10.

The object 1 emits directly or indirectly a near field wave $W_{NF}$ towards the lens 10. The lens 10 converts or transforms such near field wave $W_{NF}$ into a far field wave $W_{FF}$ by the TEM modes of the lens, as explained above.

The lens is identical to the one of the first embodiment.

The plurality of transducers 20, remote from the lens, receives the far field wave $W_{FF}$ from the lens 10. Each transducer $T_j$ delivers a transducer signal $t_j(t)$ to the control unit 30.

The control unit 30 computes object signals $o_i(t)$ at each points $P_i$ by the following formulas:

$$o_i(t) = h_{ij}(t) * t_j(t)$$

where $h_{ij}(t)$ are predetermined filters designed to determine the near field wave on the point of index-number i, such predetermined filters being determined in an initial learning step as described above, and

* is the convolution product operator.

The image of the object is then build with the values at the origin time $o_i(t)$ of the object signals $o_i(t)$.

Another experiment was carried out to demonstrate the imaging ability of the lens.

The same square periodic lattice or grid of wires is used, with antenna element at all the points $P_i$. The same learning step, is used to determine the impulse responses $g_{ij}(t)$ and the predetermined filters used in the control unit 30. The predetermined filters $h_{ij}(t)$ are for example equal to the impulse responses $g_{ij}(t)$.

Figure 6:
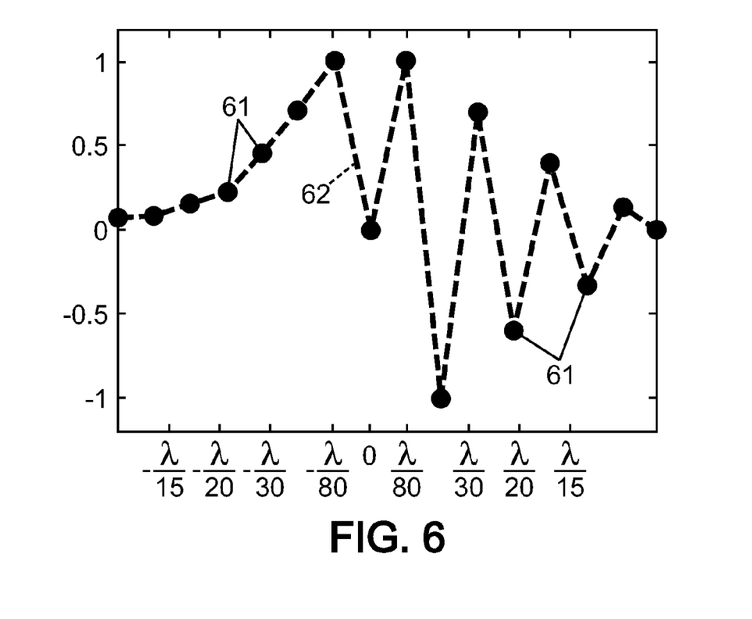
FIG. 6 is a plot concerning an imaging experience of the object by the system of FIG. 1.

Then, a different predetermined excitation is generated at each point Pi in from of the lens 10, and the control unit 30 computes the object signal $o_i(t)$ and the values of the image of the object 1. In the plot of FIG. 6, the x-axis is the plurality of points Pi on the object, and the y-axis is the amplitude of a signal. The points 61 of FIG. 6 represent said excitation and the curve 62 of FIG. 6 represent the calculated image of the object 1.

The good agreement between these points and the curve demonstrates that the system is able to computes a precise image of the object 1 comprising uncorrelated pixels, so that the image has a resolution lower than $\lambda/80$.

Such system for imaging an object may then be used for imaging precisely a small object as an electronic microscope. However, such system does not need to move a tip above the surface of the object, as is absolutely necessary in a scanning tunnelling microscope.

A second embodiment of the system for imaging may be adapted for optical waves. Such optical system would have the same changes compared to the electromagnetic device as explained above.

A third embodiment of the system for imaging may be also adapted for acoustical waves.

As an improvement of all the previous embodiments and variants, the system may also comprise at least one lens transducer incorporated inside the lens 10 and connected to the control unit 30.

This lens transducer may be fed with a lens signal l(t) provided by the control unit 30 to modify the properties of the lens 10. For example, in case of an electromagnetic device, the lens transducer may generate an electric field inside the lens 10 that modifies the TEM modes as desired.

This lens transducer may also provide a lens signal l(t) to the control unit 30 to retrieve information inside the lens 10. Such lens signal may be used by the control unit as the other transducers are treated. For example, the image building of an object may be improved by such added information.

The invention claimed is:

1. A system for illuminating an object with a wave, comprising:
   a lens for converging a far field wave to a near field wave, said lens comprising a medium and a plurality of resonator elements incorporated inside said medium, each resonator element being spaced from an other resonator element inside the medium of a distance lower than a first distance $d_1$, and having:
   a width $w_R$ in a direction to a neighbour resonator element lower than said first distance $d_1$,
   a length $l_R$ in an other direction, and
   a resonance frequency $f_R$ corresponding to a resonance wavelength $\lambda_R$,
   a plurality of transducers remote from said lens, said plurality of transducers having a transducer wavelength bandwidth $\Delta\lambda_T$ and being adapted to emit the far field wave towards the lens based on signals $t_j(t)$ of index-number j, and
   a control unit connected to said transducers, said control unit providing signals $t_j(t)$ of index-number j to the transducers so that the transducers emit a far field wave corresponding to the signals and so that the lens produces a desired near field wave, said desired near field wave being focused on at least a plurality of points $P_i$ of index-number i belonging to an object so as to illuminate said object with said desired near field wave, wherein:
   the resonance wavelength $\lambda_R$ is comprised between $\lambda_{min}$ and $\lambda_{max}$ inside the transducer wavelength bandwidth $\Delta\lambda_T$ so that the near field wave spreads into a desired wavelength bandwidth $\Delta\lambda_D$ between $\lambda_{min}$ and $\lambda_{max}$,
   the first distance $d_1$ is lower than $\lambda_{max}/5$ so that said resonator elements are coupled to each other, and
   the system further comprises positioning means adapted for positioning at least one point $P_i$ of the object at a distance of at least one resonator element lower than a second distance $d_2$, said second distance $d_2$ being lower than $\lambda_{max}/5$.

2. The system according to claim 1, wherein the desired near field wave is focused simultaneously on said plurality of points.

3. The system of claim 1, wherein the width $w_R$ is lower than $d_1/5$.

4. The system of claim 1, wherein the first distance $d_1$ is lower than $\lambda_{max}/20$.

5. The system of claim 1, wherein the second distance $d_2$ is lower than $\lambda_{max}/20$.

6. The system of claim 1, wherein the length $l_R$ of the resonator element is roughly equal to $\lambda_R/2$ or a multiple of it.

7. The system of claim 1, wherein the resonator elements have a plurality of lengths so that the lens has a plurality of resonance wavelengths $\lambda_R$ between $\lambda_{min}$ and $\lambda_{max}$.

8. The system of claim 1, further comprising at least one lens transducer incorporated inside said lens, wherein said lens transducer is fed with a lens signal l(t), the control unit is connected to said lens transducer and provide the lens signal l(t).

9. The system of claim 1, wherein the control unit computes the signals $t_j(t)$ of the transducer of index-number j by one of the following formulas:

$$t_j(t) = h_{ij}^{-1}(t) * o_i(t) \text{ in time domain, and}$$

$$t_j(t) = IFFT(H_{ij}^{-1}(\omega) \cdot O_i(\omega)) \text{ in frequency domain,}$$

where
   $o_i(t)$ is an object signal corresponding to the desired near field wave on the object,
   $h_{ij}(t)$ are predetermined filters designed to focus the near field wave on the point of index-number i of the object,
   t is a time value,
   * is the convolution product operator,
   $O_i(\omega)$ is a Fourier transform of the object signal $o_i(t)$,
   $H_{ij}(\omega)$ is a Fourier transform of the predetermined filters $h_{ij}(t)$,
   IFFT is an inverse Fourier transform, and
   $\omega$ is a frequency pulsation equal to $2.\pi.f$ where f is a frequency of the desired near field wave.

10. The system of claim 9, wherein the predetermined filters $h_{ij}(t)$ are one of:
   delay filters so that the control unit computes beamforming formulas; and
   filters determined on basis of an impulse response $g_{ij}(t)$ between the point of index-number i of the object and the transducer of index-number j; and
   temporal inversion $g_{ij}(-t)$ of an impulse response $g_{ij}(t)$ between the point of index-number i of the object and the transducer of index-number j.

11. The system of claim 10, wherein the impulse response $g_{ij}(t)$ is determined during an initial learning step wherein at least one calibration transducer is positioned in the place of the object at each of said points of index-number i and at least a calibration signal is exchanged between said calibration transducer and the transducer of index-number j.

12. The system of claim 10, wherein the impulse response $g_{ij}(t)$ is determined during an initial learning step wherein a simulation tools running on a computer is filled in with a model of the system and wherein said model comprises at least one calibration transducer positioned in the place of the object at each of said points of index-number i and at least a calibration signal is exchanged between said calibration transducer and the transducer of index-number j.

13. The system of claim 1, wherein the transducers are electromagnetic antenna elements adapted to emit an electromagnetic far field wave and the resonator elements are conductive wires adapted to receive an electromagnetic far field wave and to emit an electromagnetic near field wave.

14. The system of claim 1, wherein the transducers are photo emitters adapted to emit a far field wave of light and the resonator elements are conductive elements adapted to receive said far field wave of light and to emit a near field wave of light.

15. The system of claim 14, wherein the conductive elements are nanoparticles or conductor elements having a width $w_R$ lower than 50 nm.

16. The system of claim 15, wherein the conductive elements comprise active materials adapted to receive a wave at a first wavelength $\lambda_1$ and to emit a wave at a second wavelength $\lambda_2$ different to said first wavelength $\lambda_1$.

17. The system of claim 16, wherein said active materials are one of quantum dots, and dyes, and fluorescent molecules.

18. A system for imaging an object with a wave, comprising:
   a lens for diverging a near field wave to a far field wave, said lens comprising a medium and a plurality of resonator elements incorporated inside said medium, each resonator element being spaced from an other resonator element of a distance lower than a first distance $d_1$, and having:
- a resonance frequency $f_R$ corresponding to a resonance wavelength $\lambda_R$,
- a width $w_R$ in a direction to a neighbour resonator element lower than said first distance $d_1$, and
- a length $l_R$ in an other direction,
  - a plurality of transducers remote from said lens, said plurality of transducers having a transducer wavelength bandwidth $\Delta\lambda_T$ and being adapted to receive the far field wave from the lens and to provide signals $t_j(t)$ of index-number j representative to said far field wave, and
  - a control unit connected to said transducers, said control unit being fed with the signals $t_j(t)$ of index-number j from the transducers, and adapted to determine therewith the near field wave at a plurality of points $P_i$ of index-number i belonging to an object so as to obtain an image of said object, wherein:
the resonance wavelength $\lambda_R$ is comprised between $\lambda_{min}$ and $\lambda_{max}$ inside the transducer wavelength bandwidth $\Delta\lambda_T$, so that the far field wave spreads into a desired wavelength bandwidth $\Delta\lambda_D$ between $\lambda_{min}$ and $\lambda_{max}$,
the first distance $d_1$ is lower than $\lambda_{max}/5$ so that the resonator elements are coupled to each other, and
the system further comprises positioning means adapted for positioning at least one point of the object at a distance of at least one resonator element lower than a second distance $d_2$, said second distance $d_2$ being lower than $\lambda_{max}/5$.

19. The system of claim 18, wherein the near field wave is determined simultaneously on said plurality of points.

20. The system of claim 18, wherein the width $w_R$ is lower than $d_1/5$.

21. The system of claim 18, wherein the first distance $d_1$ is lower than $\lambda_{max}/20$.

22. The system of claim 18, wherein the second distance $d_2$ is lower than $\lambda_{max}/20$.

23. The system of claim 18, wherein the length $l_R$ of the resonator element is roughly equal to $\lambda_R/2$ or a multiple of it.

24. The system of claim 18, wherein the resonator elements have a plurality of lengths so that the lens has a plurality of resonance wavelengths $\lambda_R$ between $\lambda_{min}$ and $\lambda_{max}$.

25. The system of claim 18, further comprising emitting means for emitting an emitted wave having wavelengths comprised between $\lambda_{min}$ and $\lambda_{max}$ towards said object, so that a near field wave is refracted or reflected from said object, said near field wave comprising wavelengths comprised between $\lambda_{min}$ and $\lambda_{max}$ and being diverged by the lens into a far field wave.

26. The system of claim 18, further comprising emitting means connected to said object, so that the object itself emits a near field wave comprising wavelengths comprised between $\lambda_{min}$ and $\lambda_{max}$ and being diverged by the lens into a far field wave.

27. The system of claim 18, further comprising at least one lens transducer incorporated inside said lens, wherein said lens transducer is fed with a lens signal l(t), the control unit is connected to said lens transducer and provide the lens signal l(t).

28. The system of claim 18, wherein the control unit:
receives signals $t_j(t)$ from the transducers,
calculates object signals $o_i(t)$ at each of the points of index-number i by the following formula:

$$o_i(t)=h_{ij}(t)*t_j(t)$$

where
$h_{ij}(t)$ are predetermined filters designed to determine the near field wave on the point of index-number i,
* is the convolution product operator, and
builds an image of the object with the values at origin time $o_i(0)$ of the object signals $o_i(t)$ at each of the points of index-number i.

29. The system of claim 28, wherein the predetermined filters $h_{ij}(t)$ are one of:
delay filters so that the control unit computes beamforming formulas; and
filters determined on basis of an impulse response $g_{ij}(t)$ between the point of index-number i of the object and the transducer of index-number j; and
temporal inversion $g_{ij}(-t)$ of an impulse response $g_{ij}(t)$ between the point of index-number i of the object and the transducer of index-number j.

30. The system of claim 29, wherein the impulse response $g_{ij}(t)$ is determined during an initial learning step wherein at least one calibration transducer is positioned in the place of the object at each of said points of index-number i and at least a calibration signal is exchanged between said calibration transducer and the transducer of index-number j.

31. The system of claim 29, wherein the impulse response $g_{ij}(t)$ is determined during an initial learning step wherein a simulation tools running on a computer is filled in with a model of the system and wherein said model comprises at least one calibration transducer positioned in the place of the object at each of said points of index-number i and at least a calibration signal is exchanged between said calibration transducer and the transducer of index-number j.

32. The system of claim 18, wherein the transducers are electromagnetic antenna elements adapted to receive an electromagnetic far field wave and the resonator elements are conductive wires adapted to receive an electromagnetic near field wave and to emit an electromagnetic far field wave.

33. The system of claim 18, wherein the transducers are photo receivers adapted to receive a far field wave of light and the resonator elements are conductive elements adapted to receive a near field wave of light and to emit a far field wave of light.

34. The system of claim 33, wherein the conductive elements are nanoparticles or conductor elements having a width $w_R$ lower than 50 nm.

35. The system of claim 34, wherein the conductive elements comprise active materials adapted to receive a wave at a first wavelength $\lambda_1$ and to emit a wave at a second wavelength $\lambda_2$ different to said first wavelength $\lambda_1$.

36. The system of claim 35, wherein said active materials are one of quantum dots, and dyes, and fluorescent molecules.

37. A method for illuminating an object with a wave, wherein:
resonator elements are incorporated inside a medium to form a lens for converging a far field wave to a near field wave, said resonator elements being spaced from an other resonator element inside the medium of a distance lower than a first distance $d_1$, and having:
a width $w_R$ in a direction to a neighbour resonator element lower than said first distance $d_1$,
a length $l_R$ in an other direction, and
a resonance frequency $f_R$ corresponding to a resonance wavelength $\lambda_R$, said resonance wavelength $\lambda_R$ being comprised between $\lambda_{min}$ and $\lambda_{max}$, and the first distance $d_1$ being lower than $\lambda_{max}/5$ so that said resonator elements are coupled to each other, at least one point $P_i$ of the object is positioned at a distance of at least one resonator element lower than a second distance $d_2$, said second distance $d_2$ being lower than $\lambda_{max}/5$, a plurality of transducers are positioned remote from said lens, said plurality of transducers having a transducer wavelength bandwidth $\Delta\lambda_T$ comprising $\lambda_{min}$ and $\lambda_{max}$, and being adapted to emit the far field wave towards the lens based on signals $t_j(t)$ of index-number j, and signals $t_j(t)$ of index-number j are provided to the transducers so that the transducers emit a far field wave corresponding to the signals and so that the lens produces a desired near field wave, said near field wave having wavelengths comprised into a desired wavelength bandwidth $\Delta\lambda_D$ between $\lambda_{min}$ and $\lambda_{max}$, and being focused on at least a plurality of points $P_i$ of index-number i belonging to said object so as to illuminate said object with said desired near field wave.

38. A method for imaging an object with a wave, wherein:
the object emits a near field wave, and comprises
resonator elements are incorporated inside a medium to form a lens for diverging the near field wave to a far field wave, said resonator elements being spaced from an other resonator element inside the medium of a distance lower than a first distance $d_1$, and having:

a width $w_R$ in a direction to a neighbour resonator element lower than said first distance $d_1$, a length $l_R$ in an other direction, and a resonance frequency $f_R$ corresponding to a resonance wavelength $\lambda_R$, said resonance wavelength $\lambda_R$ being comprised between $\lambda_{min}$ and $\lambda_{max}$, and the first distance $d_1$ being lower than $\lambda_{max}/5$ so that said resonator elements are coupled to each other, and said far field wave having wavelengths comprised into a desired wavelength bandwidth $\Delta\lambda_D$ between $\lambda_{min}$ and $\lambda_{max}$, at least one point $P_i$ of the object is positioned at a distance of at least one resonator element lower than a second distance $d_2$, said second distance $d_2$ being lower than $\lambda_{max}/5$, a plurality of transducers are positioned remote from said lens, said plurality of transducers having a transducer wavelength bandwidth $\Delta\lambda_T$ comprising $\lambda_{min}$ and $\lambda_{max}$ and being adapted to receive the far field wave from the lens and to provide signals $t_j(t)$ of index-number j representative to said far field wave, and the signals $t_j(t)$ of index-number j are provided to a control unit to determine therewith the near field wave at a plurality of points $P_i$ of index-number i belonging to an object so as to obtain an image of said object.

* * * * *